United States Patent [19]

Sieverin

[11] 4,042,877
[45] Aug. 16, 1977

[54] INSPECTION APPARATUS AND METHOD FOR DETECTING FLAWS IN SERIALLY FED SUBSTANTIALLY CYLINDRICAL OBJECTS

[75] Inventor: Walter J. Sieverin, Buffalo Grove, Ill.

[73] Assignee: American Can Company, Greenwich, Conn.

[21] Appl. No.: 618,425

[22] Filed: Oct. 1, 1975

[51] Int. Cl.² .................................... G01R 33/12
[52] U.S. Cl. ................................. 324/37; 198/471; 209/81 R
[58] Field of Search .................. 324/34 R, 37, 40; 198/22 B, 22 R, 26, 257; 209/73, 111.8, 81 R

[56] References Cited

U.S. PATENT DOCUMENTS

| | | | |
|---|---|---|---|
| 2,979,196 | 4/1961 | Harmon | 324/34 R |
| 3,355,014 | 11/1967 | Howles | 209/73 |
| 3,447,074 | 5/1969 | Sower et al. | 324/37 |
| 3,690,487 | 9/1972 | Evans et al. | 198/257 |

Primary Examiner—Robert J. Corcoran
Attorney, Agent, or Firm—Robert P. Auber; Ira S. Dorman; George P. Ziehmer

[57] ABSTRACT

An inspection apparatus for inspecting and detecting flaws in serially fed substantially cylindrical objects. The inspection apparatus includes a notch-shaped inspection station formed by a pair of drive wheels mounted on a first shaft and a pair of discharge wheels fixedly mounted on a second shaft, parallel to the first shaft. A hook having a convex back surface is connected to and protrudes beyond the circumference of each discharge wheel. An L-shaped bracket whose body includes a sending surface and whose leg includes an infeed cradle, is mounted above the drive wheels and pivots in synchronism with the rotation of the discharge wheels. A first object in the infeed cradle is positively sent by the bracket sending surface toward the inspection station as the hook convex back surfaces are rotating up through the inspection station. The sent first object contacts the hook back surface which by its clockwise rotational motion imparts a counterclockwise rotational motion to the object while easing it into the inspection station where it is rotated and inspected for flaws by sensors mounted axially on an imaginary straight line drawn from the axial center line of the inspection station to the axial center of the first or second shaft.

32 Claims, 10 Drawing Figures

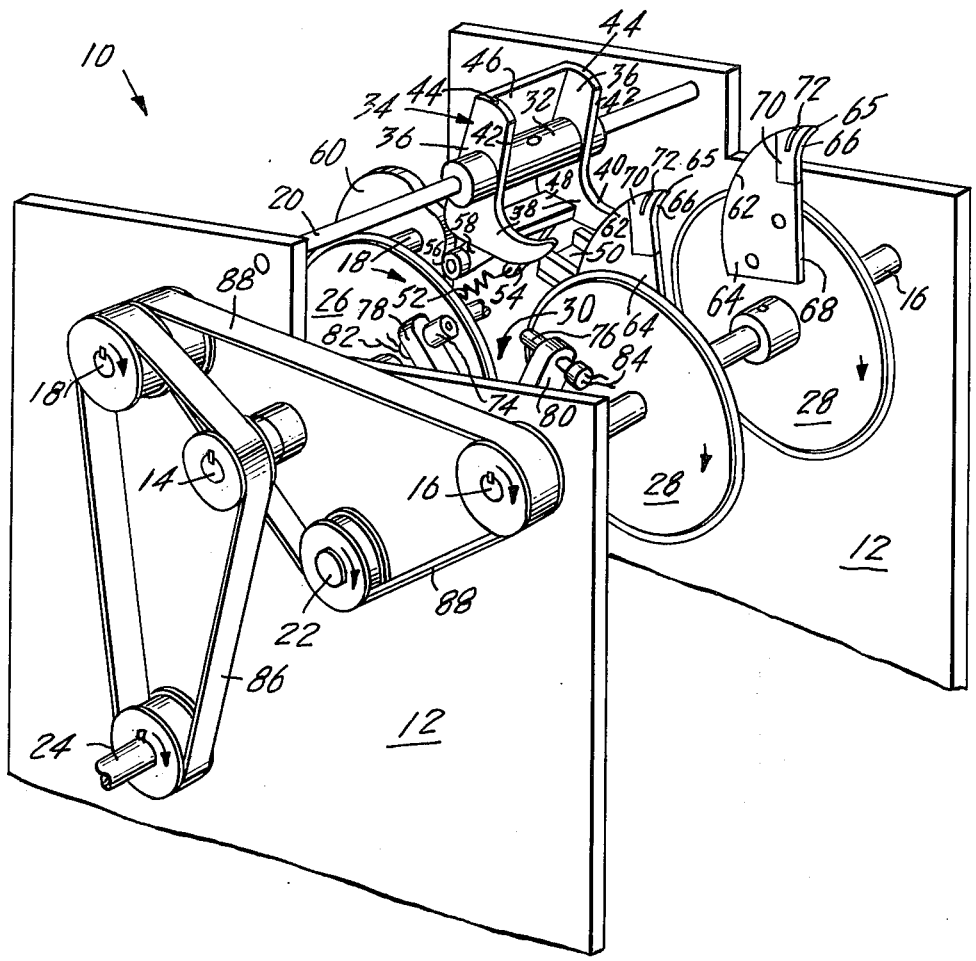
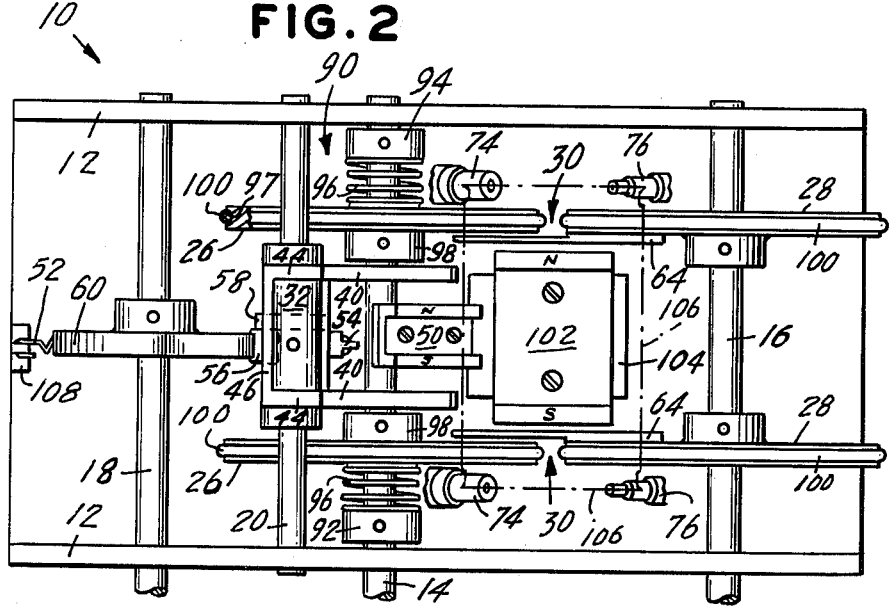

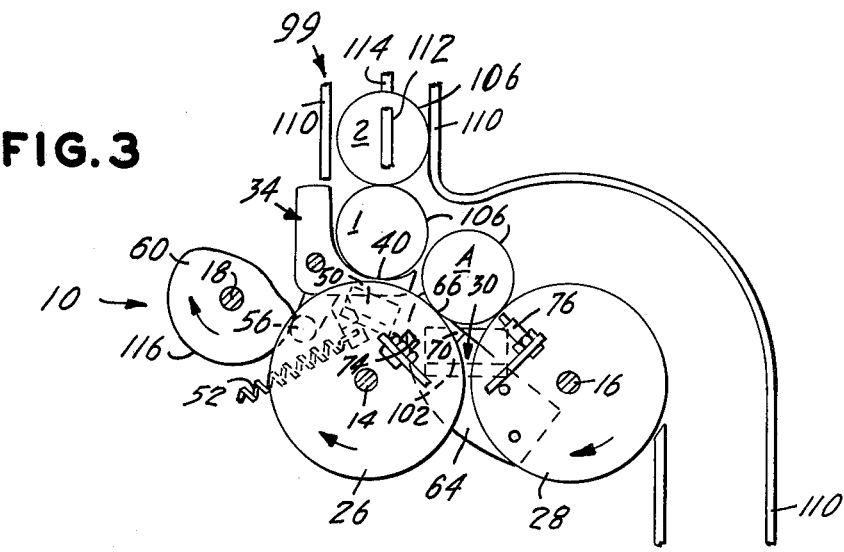
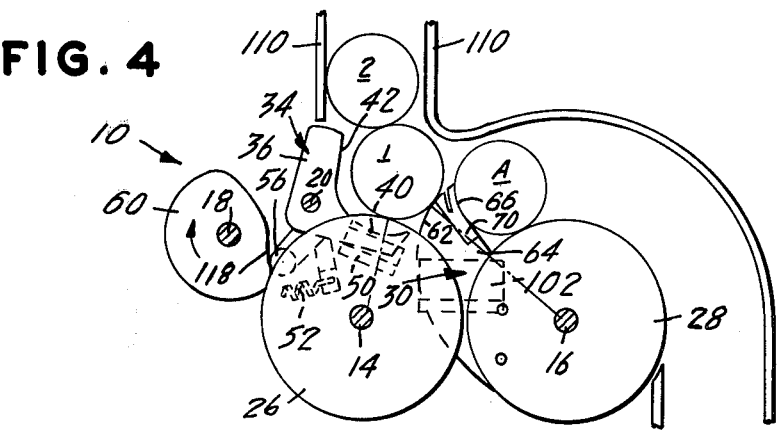
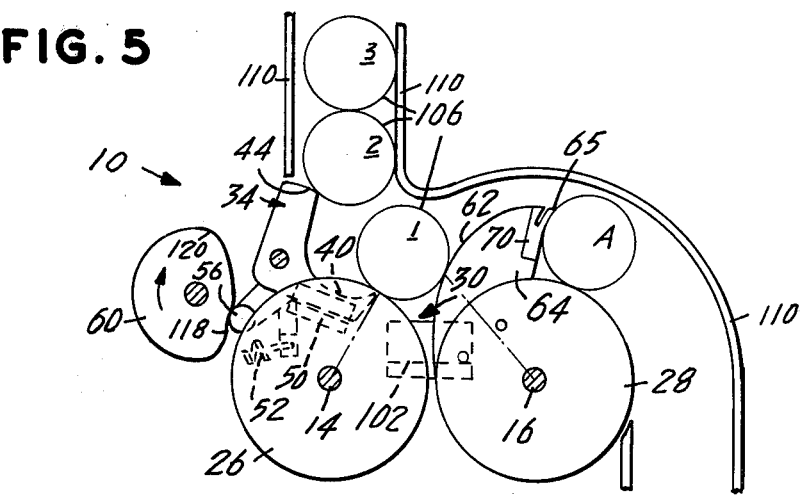

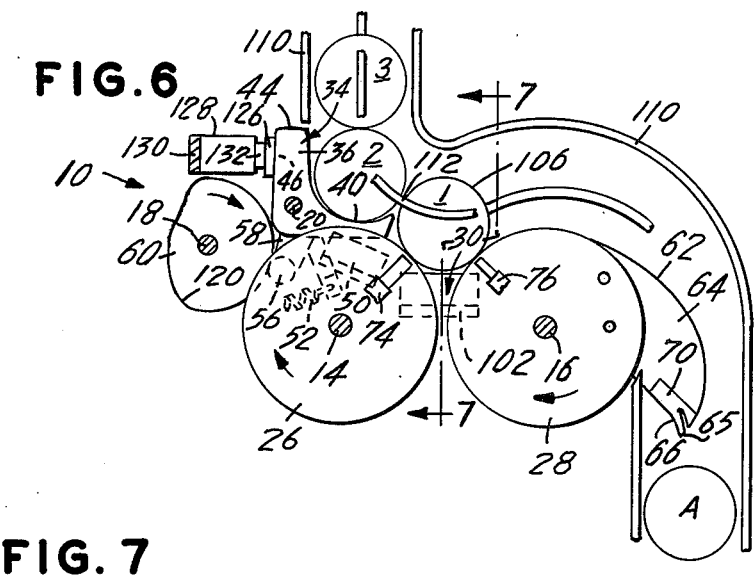
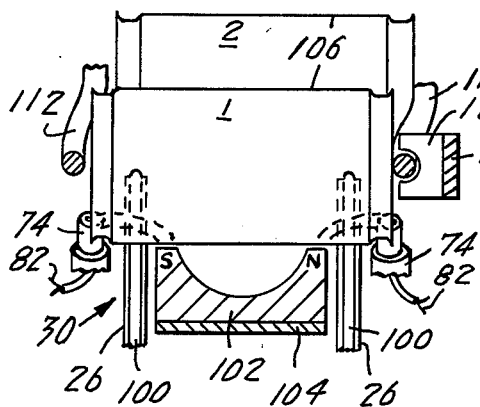
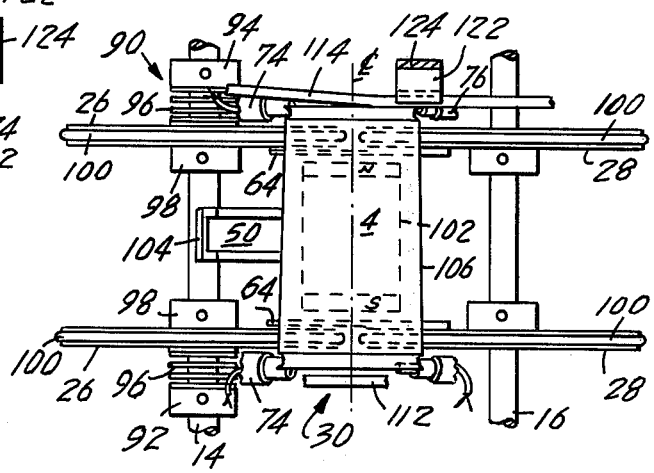
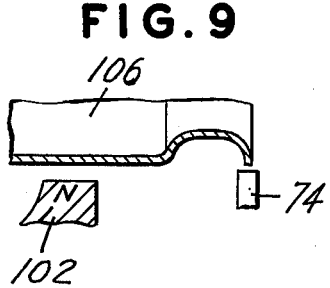
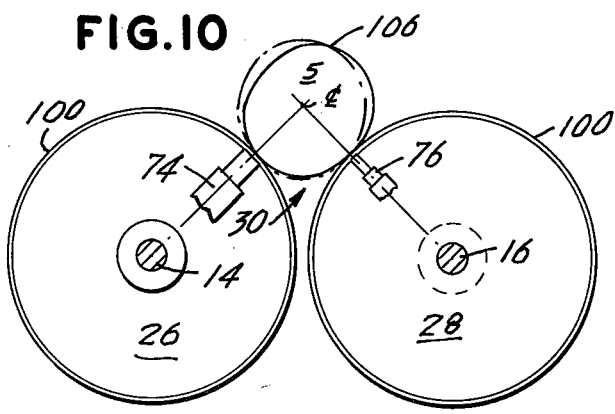

INSPECTION APPARATUS AND METHOD FOR DETECTING FLAWS IN SERIALLY FED SUBSTANTIALLY CYLINDRICAL OBJECTS

BACKGROUND OF THE INVENTION

This invention relates to the detecting of flaws in substantially cylindrical objects. More particularly, this invention relates to apparatus for rapidly and continuously feeding such objects, for example, container bodies, to an inspection station, and for inspecting them there to detect flaws in portions of their bodies such as their rims.

Apparatus for rapidly feeding a plurality of serially fed substantially cylindrical objects such as container bodies to an inspection station and for inspecting them while they are being rotated there, are well known. Such apparatus are commonly employed in the ferrous can manufacturing industry. However, such apparatus are disadvantageous for several reasons. They usually involve troublesome and complicated machinery, such as large rotating wheels or turrets having multiple peripheral pockets having mandrels for mounting the container bodies thereon, indexing mechanisms for indexing the pockets and mandrels with infeed and discharge systems involving complicated movable intermittent linkage mechanisms such as chucks for transporting the container bodies to and placing them on the mandrels. Such mechanisms are expensive and require frequent repair. Also, such apparatus are often not fully effective for detecting flaws in certain portions, such as the rims, of container or can bodies. One such apparatus inspects lap seamed beer and beverage can bodies for cracks and leaks. The can bodies usually have a flanged open end and an end closed by an integral bottom or by an end closure. The flanged can body is placed on a mandrel in a pocket, its open end is sealed and it is internally pressurized. This apparatus and procedure is often ineffective for detecting cracks in rim and flange areas because the seal used for sealing the open end abuts, covers, and prevents effective inspection of the rim and flange areas. This pressured inspection system is only useful in relation to can bodies closed at one end by an integral or separate end closure secured thereto. Rejection and disposal of a defective can body dye to say a flange crack is wasteful because it involves disposal of the integral end or end closure material, even though the end may not be defective. It also would be desirable if currently available container body testing apparatus would operate more rapidly. Another disadvantage of currently available container body inspection apparatus is that containers get damaged and there is much down time due to jams caused by irregularly-shaped, out-of-round, or otherwise damage or flawed containers. For example, a conically-shaped container having different end diameters may not be physically acceptable to or registerable in and may therefore jam in current inspection stations. This might also result in damage to an additional number of containers for failure of the apparatus to immediately shut off.

Currently available inspection apparatus tailored to inspect container body rims for flaws such as cracks, have been less than fully effective for inspecting rims of containers such as cans whose bodies and rims are slightly out-of-round, and have been totally ineffective when the bodies and rims are greatly out-of-round. The reason for this is that such sensors are only effective within a certain sensor-to-rim gap distance or sensitivity range. The prior art has been only partly successful in effectively sensing gap variations but only narrow gap variations within the sensor's overall gap sensitivity range. This partial success has been achieved by use of complicated electronic gap variation compensation circuits. Prior art detection systems are totally ineffective with respect to wide gap variations such as produced by grossly out-of-round container bodies whose rims have portions which go greatly beyond either the very narrow or the overall sensor gap sensitivity range. It would therefore be desirable to provide a detection apparatus and systems which, regardless of whether rims are slightly or grossly out-of-round, would provide only minimum gap variations within acceptable limits that are within the sensor's overall gap sensitivity range.

Objectives of the inspection apparatus of this invention are to overcome the above and other disadvantages by providing a simply designed, relatively small, trouble-free, inexpensive-to-build and operate inspection apparatus which operates continuously without use of complicated intermittent linkage mechanisms. The apparatus does not employ pressurizing and sealing means and is highly effective for inspecting rims and flanges of container bodies, especially for small imperfections such as cracks, and peaked flanges. The apparatus operates rapidly with objects spending much less total time in the inspection station. A highly significant advantage of the inspection apparatus of this invention is its capability of operating trouble-free for long periods of time, without jams and with minimal damage to containers or wastage of container materials. The apparatus effectively senses and is seldom jammed by out-of-round, irregularly shaped, damaged, or flawed containers. When a container is too mangled or otherwise cannot be passed through the apparatus, it shuts off automatically on a single container jam without damage to any subsequent containers.

Another highly significant advantage of the inspection apparatus is that it operates while maintaining a nearly uniform distance between a rotating container body, say its rim and flange edges, and a fixed adjacent detecting means. The apparatus of this invention provides a mechanical system of rotating slightly a grossly elliptical or out-of-round can bodies such that their rims only cayse minimum gap variations which are within acceptable limits that are within the sensor's overall gap sensitivity range. The apparatus is therefore capable of employing currently available sensors for inspecting and detecting flaws in cylindrical bodies regardless of whether they are slightly or grossly elliptical, or are egg shaped or are otherwise out-of-round. Sensors employed with the apparatus of this invention can be employed with a very short sensor-to-rim gap distance which allows the sensor to be highly sensitive to very small variations, for example due to slightly peaked flanges and even very tiny flange cracks and dents. The sensors are therefore capable of inspecting a container body for, and simultaneously detecting large variety of flaws which would render the two or three piece container bodies unacceptable aesthetically, or for further processing or certain end uses, such as due to their unacceptable shape, peaked flanges, body blank chips in the lap seam cement or solder, or excess cement or solder at or openings in the laps at the flange lap cross overs of lap side seamed bodies.

Numerous other objects and advantages of the invention will be apparent as it is better understood from the following description, which, taken in connection with the accompanying drawings, discloses preferred embodiments thereof.

SUMMARY OF THE INVENTION

This invention is in an inspection apparatus for inspecting and detecting flaws in each of a plurality of serially fed substantially cylindrical objects, which comprises: rotatable parallel first and second shafts, a pair of drive wheels free wheelingly mounted on first shaft, a pair of discharge wheels fixed to the second shaft, the respective drive and discharge wheels being positioned such that arcs on their circumferences cooperate to form a notch-shaped inspection station for seating a substantially cylindrical first object therein, an infeed cradle mounted above the drive wheels for initially receiving and cradling the infed first object, sending means synchronized with the rotation of the second shaft for positively sending the cradled first object from the infeed cradle to the inspection station, rotation imparting and deaccelerating means, preferably a convex back surface of a hook connected to the second shaft and synchronized with the sending means for imparting a rotary motion to while simultaneously controlledly deaccelerating the translational motion of, and easing entry of, the positively sent first object into the inspection station, discharge means, preferably a hook concave face surface, connected to and synchronized with the rotation of the second shaft such that during the controlled deacceleration, it passes through the inspection station and removes a substantially cylindrical object therefrom and discharges it from the apparatus, means for rotating the first and second shafts at a constant speed and time such that the first rotates faster than the second, coupling means preferably a slip clutch assembly, adjustably mounted on the first shaft and communicating with the drive wheels for connecting the drive wheels to the first shaft, the coupling means being adjustable to impact certain pre-set desired limited torque driving capabilities to either or both drive wheels in a manner that allows either or both drive wheels to slip with respect to the first shaft when either or both is subjected to a torque whose value exceeds the pres-set limit, and, detecting means for detecting flaws in each serially fed substantially cylindrical object while it is seated and rotated in the inspection station. Preferably, the inspection apparatus includes a pivotable L-shaped bracket wherein the sensing means is a sending surface on the bracket body, the infeed cradle is a convex cutout in the bracket leg, and the bracket includes prevent means on the head of the bracket body for preventing a second object from prematurely passing to the infeed cradle. Preferably, the apparatus also includes hold means for holding a substantially cylindrical object on the drive and discharge wheels and in the inspection station while it is being rotated and inspected therein. When the object is ferrous, preferably the hold means includes a primary magnet below the inspection station, a secondary magnet between and below the upper peripheral portions of the drive wheels, and orienting means, preferably a horseshoe-shaped magnet whose poles straddle a side guide rail and attract the rim edge of the object against the rail to hold the object in an oriented position in the inspection station. When the object is a ferrous open-ended container body the orienting means aligns the rim or flange edge of the can body with the detecting means, which preferably are magnetic sensors.

When magnetic sensors are employed for detecting flaws in the rims of ferrous container bodies, the sensors are axially aligned with and fixedly mounted on an imaginary straight line drawn from the axial center of the inspection station to the axial center point of the first or second shafts, adjacent the point of contact between the can and the wheel that is mounted on the first or second shaft, to thereby maintain a substantially uniform gap between the sensors and the can.

BRIEF DESCRIPTION OF THE DRAWINGS

FIG. 1 is a persepective view of a preferred embodiment of the inspection apparatus of this invention.

FIG. 2 is a plan view, with portions broken away, of the apparatus of FIG. 1.

FIGS. 3 through 6 are fron elevations with portions broken away, which show the operation of the inspection apparatus of this invention.

FIG. 7 is a side view with portions in cross section and with portions broken away, taken substantially along line 7—7 of FIG. 6.

FIG. 8 is a plan view of a portion of the inspection apparatus, showing a container body of non-uniform diameter oriented in the inspection station.

FIG. 9 is an enlarged view partially in section, taken of a portion of the primary magnet, container body rim and detecting means shown in FIG. 7.

FIG. 10 is a schematic side view of a portion of the apparatus of this invention showing means for maintaining a uniform distance between and out-of-round container body and the detecting meams of this invention.

DETAILED DESCRIPTION OF THE INVENTION

FIG. 1 is a perspective view of a preferred embodiment of the apparatus of this invention. More particularly, FIG. 1 shows an inspection apparatus for inspecting and detecting flaws in each of a plurality of serially fed substantially cylindrical objects. The inspection apparatus, generally designated 10 is mounted on a suitable frame having upstanding substantially parallel walls 12. Mounted in walls 12 and extending therebetween are a plurality of substantially horizontal shafts, including rotatable first and second shafts 14, 16 parallel to and spaced from each other, cam shaft 18, and, above the frist shaft, fixed bracket shaft 20. Mounted on one wal is fixed pulley shaft 22 and broken away rotatable main drive shaft 24.

Inspection apparatus 10 includes means connected to the first and second shafts for rotating them in time such that first shaft 14 rotates at a higher rate of speed than second shaft 16, such means including drive means such as motor (not shown) connected to main drive shaft 24, and motor pulley drive belt 86 engaged pulleys respectively keyed main drive shaft 24, cam shaft 18 and first shaft 14, for driving the respective shafts in synchronism. The means also includes timing belt 88 engaged about rollers affixed to cam shaft 18, second shaft 16, and free-wheeling tensioning pulley of shaft 22, for driving and rotating cam shaft 18 and secnd shaft 16 in synchronism. Because of the above means and because the motor driven pulley affixed to first shaft 14 has a smaller diameter than the motor driven pulley affixed to cam shaft 18, first shaft 14 and drive wheels 26 connected thereto rotate at a higher rotational speed than second shaft 16 and discharge wheels 28.

Free-wheelingly mounted on first shaft 14 are a pair of drive wheels 26 (one shown), and, fixedly mounted on second shaft 16 are a pair of discharge wheels 28, the respective drive and discharge wheels being separated from one another on their respective shafts and being so positioned thereon that arcs of their respective circumferences cooperate to form a notch-shaped inspection station 30 for seating a substantially cylindrical object, such as a can (not shown) therein. Drive wheels 26 drive the object into and impart a rotary motion to the object during the driving action and while the object is seated in inspection station 30. Freely mounted on fixed bracket shaft 20 is bracket collar 32 and an L-shaped bracket, generally designated 34, which includes a pair of upstanding bodies 36, each body having an outwardly extending leg 38, each of which includes an infeed cradle 40, here shown as a convex cutout. Infeed cradle 40 is mounted above drive wheels 26 for initially receiving and cradling a first infed object prior to its being seated in inspection station 30. L-shaped bracket 34 also includes sending means here shown as a sending surface 42 on body 36, the operation of the sending means being synchronized with the rotation of second shaft 16, for positively sending a cradled object from infeed cradle 40 to inspection station 30. L-shaped bracket body 36 preferably includes prevent means, here shown as a slightly arcuate head 44 at the top of body 36, the prevent means being for preventing a second object in an object infeed line (FIG. 3) above infeed cradle 40 from prematurely passing to the infeed cradle 40, that is, before the first object has been positively sent therefrom. FIG. 1 shows that L-shaped bracket 34 preferably is in the form of two bracket bodies 36 having an integral or otherwise interconnecting back 46 and an interconnecting leg brace 48, positioned below infeed cradle 40. The inspection apparatus includes hold means which include a primary magnet 102 (not shown) positioned below inspection station 30. Between bracket shaft 20 and inspection station 30, and between the respective drive wheels 26 is additional hold means in the form of a secondary magnet 50 for holding an object in contact with drive wheels 26 as the object is being positively sent from infeed cradle 40 to inspection station 30. Spring 52 is attached by connector 54 to bracket leg 38 and biases the leg downward and bracket body 36 forward toward discharge wheels 28, and keeps cam follower 56, affixed by arm 58 to L-shaped bracket 34, engaged against cam 60 mounted on rotatably driven cam shaft 18.

FIG. 1 shows that the inspection apparatus of this invention includes rotation imparting and de-accelerating means preferably in the form of a convex back surface 62 on each hook 64, each hook being connected to second shaft 16 by being connected, as by screws, to one of the respective discharge wheels 28. Convex back surface 62 is synchronized with the operation of the sending means, sending surface 42, for imparting a rotary motion to, while simultaneously controlledly de-accelerating the translational motion of and easing the entry of, the object positively sent from infeed cradle 40 to the inspection station 30. Hook 64 also includes discharge means, here discharge seat 66, which is a concave surface on face surface 68 of each hook 64. The operation and rotation of discharge seat 66 is synchronized with the rotation of second shaft 16, by the fixed connection of hook 64 to discharge wheel 28, such that with each rotation of second shaft 16 and during the controlled de-acceleration of the positively sent first object, the discharge seat 66 passes through inspection station 30 just prior to the passage therethrough of the rotation imparting and de-accelerating means, i.e. convex back surface 62, and, without use of intermittent motion mechanisms, removes a substantially cylindrical object from the inspection station, and then discharges it from the inspection apparatus. Each hook 64 has an apex 65 at the junction between its respective convex back and face surfaces 62, 68, and each hook face surface preferably includes cushioning means, here, leaf spring 70, having a groove 72 therein, for cushioning the impact of discharge seat 66 upon each object engaged by and removed from inspection station 30. Leaf spring 70 can be made of any suitable cushioning, durable material, for example nylon. While a substantially cylindrical object (not shown) is being rotated in inspection station 30, detecting means, here sensors 74, 76, mounted on walls 12 by suitable supports 78, 80 and connected to a source of electrical energy by respective wires 82, 84, are employed for detecting flaws in each serially fed substantially cylindrical object while it is seated and rotated in inspection station 30.

FIG. 2 is an enlarged plan view, with portions broken away, of the apparatus of FIG. 1. More particularly, FIG. 2 shows that cam shaft 18, bracket shaft 20 and first and second shafts 14, 16 are substantially parallel to one another, and that adjacent drive and discharge wheels 26, 28 need not be but preferably are aligned with each other to form inspection station 30. FIG. 2 also shows that inspection apparatus 10 includes coupling means including slip clutch means or assembly, generally designated 90, adjustably mounted on first shaft 14 communicating with and connected to the first shaft. The coupling means can be any suitable means which are adjustable to impart certain pre-set desired limited torque driving capabilities to either or both drive wheels 26 in a manner that allows either or both drive wheels to slip with respect to the first shaft when either or both is subjected to a torque whose value exceeds the pre-set limit. Slip clutch means of assembly 90 include collars 92, 94 axially adjustable and axially mounted, by set screws, on opposite ends of first shaft 14, and communicating with drive wheels 26 through helical springs 96 are face disks (not shown) for frictionally connecting the drive wheels to first shaft 14. Collars 92, 94 force helical spring 96 against face disks (not shown) and frictionally preload each drive wheel 26 against fixed collars 98 to establish a slip torque limit value with respect to first shaft 14 when the drive wheels are subjected to greater torque forces than are provided by the frictional preloads. As will be explained, first shaft 14 which is driven to rotate at a constant speed, slip clutch assembly 90, and drive wheels 26 are part of the kinematic drive system of this invention which allows inspection apparatus 10 to accommodate substantially cylindrical objects, for example cans which are out-of-round or have non-uniform diameters or which would otherwise be unstable when rotated in an inspection station. As will be explained, the kinematic drive system allows kinematic torque adjustments to be effected by slidingly adjusting collars 92 and/or 94 axially on first shaft 14 and fixing the collars to the shaft after establishing the torque values they will require, so that no slip occurs between drive wheels 26 and out-of-round or non-uniform diameter cans. Kinematic torque adjustments can be made for either or both drive wheels 26.

FIG. 2 shows that the outer circumferences of drive and discharge wheels 26, 28 carry by suitable means such as a groove 97, having bonded therein, high friction rings 100, which are non-slippable with respect to the wheels, and whose high friction surface prevents slippage between the objects or cans and the respective wheels. When desired, high friction rings 100 or other high friction bonded materials can provide insulation between metallic container bodies and metallic wheels. High friction rings 100 can be made of any suitable materials, preferably those highly resistant to wear, for example, polyurethanes, and natural and synthetic rubbers. Preferably the high friction ring material is resilient to compensate for small protrusions from the object or can body walls. FIG. 2 also shows that inspection apparatus 10 includes hold means for holding a substantially cylindrical object which need not be but preferably and here is shown as a flanged ferrous can body 106 (dot-dashed line) on the drive wheels and in inspection station 30 while it is being rotated and inspected therein. The hold means preferably includes horseshoe-shaped primary magnet 102 affixed to support bracket 104, preferably adjacent, below and axially aligned with center line CL of inspection station 30 (see FIG. 8), and includes secondary magnet 50 for maintaining a positively sent container body on drive wheel 26, i.e. its high friction ring 100, as the container body is being positively sent from infeed cradle 40 to inspection station 30. Primary magnet 102 has a north pole at one end of its axis and a south pole at the other of its axis. The axis extends in the same direction as but is shorter than the axis of the substantially cylindrical object, here, flanged ferrour can body 106 such that, as will be explained, primary magnet 102 induces a magnetic field through portions of ferrous can body 106 which extend axially beyond the respective primary magnet poles. Sensors 74, 76 are mounted beyond the axial length of permanent magnet 102 in substantial alignment with and in the magnetic field caused by a flaw associated with a rim portion, here, the flanged rim of ferrous body 106. Spring 52, mostly hidden by cam 60, is attached to suitable support 108.

FIGS. 3 through 6 are front elevations which show the operation of inspection apparatus 10. FIG. 3 shows a vertical gravity runway, generally designated 99, comprised of, and having an object or infeed path defined by, side guide rails 110 and end guide rails 112, 114 for guiding a plurality of horizontally-disposed vertically-aligned flanged ferrous can bodies 106 (hereafter called cans) through the runway path, and for serially feeding them to inspection apparatus 10. Of the vertical stack, the lowermost, first can, 1, is seated in infeed cradle 40 and resting on can 1 is second can, 2. L-shaped bracket 34 has already positively sent can A to the inspection station 30. Second shaft 16 has just completed a full revolution and, the entire circumference of can A has been inspected during some portion of this one revolution. Can A is about to be removed from inspection station 30 by discharge seat 66 of hook 64. First drive shaft 14 rotates in a clockwise direction at a constant but higher rotational speed than second shaft 16. The clockwise rotation of drive wheel 26 imparts a counterclockwise rotation to can A and simultaneously tends to drive it into, and keep it in inspection station 30. While can A was being rotated in inspection station 30, cam follower 56 was held by spring 52 against dwell surface 116 of cam 60. FIG. 3 shows leaf spring 70 as it is cushioning and softening hook impact with can A in inspection station 30.

FIG. 4 shows that because cam shaft 18 and second shaft 16 are synchronized, when cam follower 56 passes over cam fall surface 118, the biasing force of spring 52 pivots L-shaped bracket 34 and its body 36 clockwise toward inspection station 30. Infeed cradle 40 pivots downward below the upper periphery of drive wheels 26 and places can 1 in contact with a tangent point on the periphery of drive wheels 26. The pivoting of L-shaped bracket 34 also causes its body 36 and sending surface 42 to kick and positively send can 1 from infeed cradle 40 to inspection station 30. Because the rotational speed of cam shaft 18 and the timing of the pivoting of L-shaped bracket 34 are synchronized with the rotational speed of second shaft 16, hook 64 is interposed between positively sent can 1 and inspection station 30 such that can 1 contacts or engages hook convex back surface 62, which, by its clockwise rotation and movement, imparts counterclockwise rotational motion to can 1 while simultaneously controlledly deaccelerating the can's translational motion and while simultaneously easing its entry into inspection station 30. Just before can 1 engages convex back surface 62, hook discharge seat 66 engages and starts to remove inspected can A from inspection station 30. Discharge seat 66 continues to move can A clockwise up into a discharge path defined by an arcuate portion of side guide rail 110, whose arc corresponds to the outer periphery of discharge wheel 28.

FIG. 5 shows that the continued rotational motion of discharge wheel 28 and of hook 64 has moved can A further away from inspection station 30. The clockwise rotational movement of hook convex back surface 62, has continued to impart a counterclockwise rotation to can 1 and simultaneously eased and allowed it to move further toward inspection station 30, because the radii extending from axial center of shaft 16 to tangent points adjacent apex 65 gradually decrease in length as they move through tangent points along the downward slope of the convex back surface to the point where it meets the outer circumference of discharge wheel 28, where the radius is that of discharge wheel 28.

FIGS. 4 and 5 show that the interposition of hook convex back surface 62 between the path of positively sent can 1 and inspection station 30, the hook rotational motion and the rotational driving of the can by drive wheels 26 into contact with tangent points along convex back surface 62 which are gradually progressively closer to inspection station 30, have the effect of providing an intermediate, preliminary or introductory notch station which moves gradually toward, into and from notch-shaped inspection station 30. This allows for very high speed yet stable and controlled transfers of cans from infeed cradle 40 to inspection station 30. While being transferred, the can has a minimum of slip, skid, bounce or jitter. Also, the can is already rotating at the desired speed for inspection at the time it is seated in the inspection station. Once it is in the inspection station, the can does not slip, skid, bounce or jitter.

CAn stability and lack of slippage during transfer and during rotational seating in inspection station 30, is believed explainable as follows. There would be stability and no slippage if a can were seated in an inspection station formed by rotating wheels fixed to their shafts and of the same diameter or circumference and the same rotational speed because the velocity of tangent points on the circumference of all the drive wheels which would contact on side of the can body would be identical to the velocity of tangent points on the circumference of the discharge wheel which would contact the other side of the can body. Thus, there would be stability and no slippage because the torque forces on the can would be equal since they would be applied through radii of equal length at tangent point of equal velocity. In view of this, it would be expected that instability and slippage would occur during transfer of a non-uniform diameter or conically-shaped cans into inspection station 30 because, the can body would be subjected to different torque forces applied by tangent points of different and changing velocities due to the differences and variations in length of the drive wheel radius and the radii extending to convex back surface 62. Instability and slippage would also be expected during can rotational seating in inspection station 30, if the can was conical in shape. However, these problems of instability and slippage are obviated by the kinematic drive system of the apparatus of this invention which provides kinematic torque adjustment capability. Drive wheels 26 are not fixed to first shaft 14 and, though they could have different radii, and though first shaft 14 has a higher rotational speed than second shaft 16, slip clutch assembly 90, allows either or both drive wheels 26 to slip at a pre-set torque limit rather than allowing the can to slip so that when torque values greater than the pre-set limit are applied to either or both drive wheels, either or both wheels will slip and can 1 will remain stable and not slip, skip or jump as it is transferred into or rotated in inspection station 30. Back slippage of drive wheels 26 help drive can bodies into inspection station 30. Required torque values can be established by axially moving either or both collars 92, 94 on first shaft 14 and keying they thereto where desired to thereby adjust the respective torque values of the drive wheels so that they will always be sufficiently equal to those provided by the discharge wheel and hook 64, such that no slippage occurs between drive wheels 26 and can 1. Thus, the kinematic drive system of this invention provides for self variable angular velocities of tangent points on the drive wheels depending on where a can is on the hook convex back surface. This allows the drive wheels to slow down and slip on first shaft 14, such that the velocities of their tangent points and those on convex back surface 62, and the torque forces applied therethrough are equal.

Referring again to FIG. 5, secondary magnet 50 attracts ferrous can 1 and helps keep the can in contact with drive wheels 26. Secondary magnet 50 also draws can 1 down convex back surface 62. Primary magnet 102 provides an attractive force which helps keen can 1 in contact with the drive wheels and convex back surface 62, and thereby helps to impart a rotary motion to the container body as it rolls downwardly along back surface 62. FIG. 5 shows that as L-shaped bracket 34 pivots clockwise to its furthest point, bracket body head 44 juts into the gravity runway infeed path between side guide rails 110, engages the underneath of can 2 and prevents it from prematurely passing or dropping from the infeed line on to infeed cradle 40.

Between the views shown in FIGS. 5 and 6, cam follower 56 passes over rise surface 120 which causes L-shaped bracket 34 to pivot counterclockwise back to the left. This action takes bracket body head 44 out of engagement with can 2, allows can 2 to drop onto infeed cradle 40, and can 3 to rest on cradled can 2 (as shown in FIG. 6). FIG. 6 shows that can 1 has been fully seated in inspection station 30 since the time that it lost contact with convex back surface 62. Can 1 will remain in and be rotated in inspection station 30 while it is in contact with the circumference of discharge wheels 26 and 28, until hook discharge seat 66 again passes through and removes the can from the inspection station. While can 1 is rotating in inspection station 30, it can be inspected by any suitable detecting means employed in any suitable location for detecting flaws in substantially cylindrical objects. As shown in FIG. 2, when the flaws to be detected are in rim portions of can bodies such as in the flanges of flanged ferrous container bodies 106, sensors 74, 76 are preferably magnetic sensors. As shown in FIGS. 2, 7 and 8, sensors 74, 76 preferably are aligned with and positioned under the rims or flange edges of flanged container body 106.

One full revolution of discharge wheel 28 equals one inspection cycle. The cycle includes an introductory portion when the can is in contact with hook convex back surface 62, a settling portion for settling the can in inspection station 30 from when it leaves hook convex back surface 62 until discharge wheels 28 are in the position shown in FIG. 6, and an inspecting and detecting portion, while discharge wheels 28 are rotating the roughly 180° from their FIG. 6 to their FIG. 3 positions, when discharge seat 66 engages an inspected can to remove it from the inspection station. It is to be noted that although other cycles can be employed as desired, it is preferred to incorporate a settling portion in detection systems wherein accuracy of detection depends on the cans being highly stable while they are being inspected. FIG. 6 shows that the rotation of discharge wheels 28, the configuration and dimensions of hook 64 and of guide rails 110, and gravity allow inspection apparatus 10 to discharge inspected can A without use of any intermittent motion mechanisms. FIG. 6 shows that can A leaves discharge seat 66 when the seat passes through the horizontal. FIG. 6 also shows that back surface 46 of L-shaped bracket 34 can have a ferrous plate 126 affixed thereto, such that, when inspection apparatus 10 is to be shut off, such as when there are only a few cans left in the vertical can stack, coil 128 mounted in support 130 can be electrically energized to cause pole 132 to attract plate 126 against itself to thereby retain bracket 34 in the open position until the apparatus is again turned on. This prevents situations wherein a can might be jammed between bracket body 36 and right side guide rail 110.

FIG. 7 is a side view with portions in cross section and portions broken away, taken substantially along line 7—7 of FIG. 6. More particularly, FIG. 7 shows that inspection apparatus 10 can include orienting means, here a horseshoeshaped magnet 122, mounted onto a support 124 such that the magnet poles straddle and magnetically attract ferrous can 1 against an abutting surface such as rear end guide rail 114 to axially orient the can in the inspection station. When, as in FIG. 7, sensors 74, 76 are employed for detecting for example cracks in the flanges of a flanged ferrous can 1, magnet 122 radially and axially aligns the flange with the sensing portion of the sensors, which are connected by wires 82 to suitable electronic means for inspecting and detecting flaws and for differentiating and separately processing flawed cans. FIG. 7 clearly shows that primary magnet 102 attracts rotating can 1 and thereby holds it in inspection station 30 in contact with high friction rings 100. FIG. 7 and 9 clearly show that the magnet's north and south poles are at the ends of its axis, which extends in the same direction as but is shorter than the axis of can 1, and that the magnet induces a magnetic field axially outward of the poles through portions of ferrous can 1 axially beyond the poles, such that the magnetic lines of flux pass out of the can flange edge directly into sensors 74 (and 76, not shown) also positioned beyond the axial length of the magnet. When ferrous objects are being inspected and magnetic fields are being induced therethrough, the sensors are capable of sensing disturbances or changes in magnetic fields. Thus, sensor 74, 76 detect changes in the magnetic field caused by a flaw associated with the rim or the flange portion as ferrous can 1 is rotated in inspection station 30. FIG. 7 also shows a slight gap between front end guide rail 112 and the adjacent end of can 1. This gap allows for variations in the axial length of container bodies. Rear end guide rail 114 is bent slightly from rear to front to direct cradled can 2 against, such that it travels along, guide rail 114 to provide early flange edge-guide rail contact before can 2 enters and is seated in inspection station 30.

FIG. 8 is a plan view of a ferrous can 4 of nonuniform diameter or conical shape seated in inspection station 30 and oriented therein by magnet 122 of FIG. 7. FIG. 8 shows that magnet 122 is offset from the axis of can 4 and from center line CL of inspection station 30 such that the straddling poles of magnet 122 are adjacent and attract a portion of the rim or flange of can 4. Magnet 122 can be moved along rail 114 to permit adjustment of the force of attraction between the magnet and can 4. The diameter of can 4 varies at its respective open end portions, the shorter diameter being against rear end guide rail 114 and the longer one near front end guide rail 112.

The inspection apparatus of this invention is highly suitable for handling such conically shaped non-uniform diameter cans because its kinematic drive system permits kinematic torque adjustments to be made for either or both drive wheels 26 with respect to each end of can body 1. If each drive wheel 26 was affixed to first shaft 14 and rotating at the same speed, each end of can body 4 would be driven to rotate at a different speed. The can would be unstable because of changes in frictional drive torque values from kinematic to static and vice versa for either end of the can body. The kinematic drive system partially solves this problem because slip clutch assembly 90 allows the obtaining of certain desired limited slip torque values for each respective drive wheel. This compensates for the aforementioned changes in frictional drive torque values required by the body of can 4. The diameter at each end of can 4 dictates the speed at which each drive wheel rotates.

FIG. 9, an enlarged cross section of portions of FIG. 7, shows that the can body flange edge is aligned with sensor 74 and that magnetic lines of flux travel outward from the poles of primary magnet 102 axially through the marginal end portion of the can body, and out of its flange edge and into sensor 74.

FIG. 10 is a schematic side view of a portion of the apparatus of this invention showing means for maintaining uniform distance betwen an out-of-round container body 5 and the detecting means of this invention. More particularly, FIG. 10 shows that each sensor 74, 76 is mounted axially on an imaginary straight line drawn from the axial center of inspection station 30 to the axial center point of first or second shafts 14, 16. The axial center of inspection station 30 here means the axial center of a theoretical perfectly round cylindrical object of a certain diameter seated in the inspection station such that it contacts each respective drive and discharge wheels 26, 28. Since each drive and discharge wheel is a circle and the radial distance between the circumference of each wheel and its top edge, here the top edge of high friction ring 100, is uniform, when a sensor is mounted on the imaginary line in a fixed position relative to the outer circumference of ring 100, the sensor will be a fixed uniform distance from the portion of the object which contacts the outer circumference of ring 100. As long as such contact is maintained, the change in distance between the rim or flange edge and the sensor depends on the radial distance from the object body wall portion which contacts ring 100 and the rim or flange edge. For can bodies, this is a controlled dimension which is minimal and almost always within acceptable limits that are within the overall gap sensitivity range of currently available suitable sensors. Such continual contact is maintained even with irregularly shaped, out-of-round, elliptical, egg shaped, or conically shaped objects or cans by the hold means of this invention, and by the kinematic torque wheel drive system of this invention, wherein the drive wheels and their high friction rings 100 drive a can downwardly into the notch-shaped inspection station 30, and wherein either or both drive wheels 26 have the ability to slip to prevent a can body from slipping, skidding or jumping in the inspection station. Thus, the kinematic torque wheel drive system of this invention not only allows the inspection apparatus of this invention to accommodate and rotate various irregularly shaped cans but also maintains their body walls in continual contact with the drive and discharge wheels, i.e. their rings 100, during their rotation and inspection in the inspection station.

Hooks 64 need not be connected to each discharge wheel 28, but they can be directly connected to second shaft 16 or to a separate shaft if desired, so that the same discharge wheels can be employed for inspecting can lots of different diameters, and so that the rotational speed of the hook can be increased over that of discharge wheel 28, for example, to more quickly remove inspected cans from inspection station 30. Also, there need not be two hooks. One hook of a suitable dimension is sufficient. The hook need not be separate from discharge wheel but the discharge wheel can be profiled to include an integral hook. The contour of hook convex back surface 62 is determined by the characteristics of the substantially cylindrical object to be inspected, such as its diameter, weight, mass, by the relative translational motion and deacceleration values, by the diameter of drive wheels 26 and by the attractive forces produced by the hold means, here primary magnet 102. Preferably, the contour or profile is that which provides the fastest and most stable introduction of the can into inspection station 30.

The hold means of this invention includes primary magnet 102 below the inspection station 30 for holding a can on the drive wheels and in the inspection station while it is being rotated and inspected.

The detecting means or sensors 74, 76 of this invention can be any suitable means for inspecting and detecting flaws in substantially cylindrical objects, depending on the types of materials of which the objects are made, and the types of flaws to be detected. For those flaws associated with the marginal end portiona, rims or flanges of ferrous objects such as two or three piece steel can bodies, at least one of the sensors is a magnetic sensor. Magnetic sensors sense disturbances in a magnetic field caused by flange cracks or other flaws. The sensed disturbance is transformed, by suitable means, into an electrical signal which is processed by suitable means to determine whether the disturbance is an acceptable one. If the disturbance is unacceptable the container body is discharged accordingly. Although more than one magnetic sensor can be employed at one end of a ferrous can body, only one is needed. Preferably, one sensor is magnetic, say sensor 74, and the other is a suitable non-magnetic one such as an optical sensor eddy current system for detecting non-magnetic features and aspects of the can body. For example, sensor 74 can be a magnetic sensor which, by virtue of its axial alignment on the theoretical straight line according to this invention and by virture of its consequent short sensor-to-rim gap and therefore high sensitivity, is capable of detecting very small flange peaks, cracks and dents, sensor 76, can be a non-magnetic sensor such as an optical sensor which provides complimentary or supplementary non-magnetic flaw detection. Optical sensors can be used, for example, to detect openings in the laps at the ends of lapped can bodies.

Although the drawings disclose flanged cans open at each end, and show pairs of sensors at each open end, it is understood that for two-piece container bodies having one open end, sensors would be positioned to detect flaws in the flange of the open end.

It is thought that the invention and many of its attendant advantages will be understood from the foregoing description and it will be apparent that various changes may be made in the form, construction and arrangement of parts of the apparatus mentioned herein and in the steps and order of accomplishment of the method described herein, without departing from the spirit and scope of the invention or sacrificing all of its material advantages, the apparatus and method hereinbefore described being merely a preferred embodiment thereof.

I claim:

1. An inspection apparatus for inspecting and detecting flaws in each of a plurality of serially fed substantially cylindrical objects, which comprises:
   rotatable first and second shafts parallel to and spaced from each other,
   a pair of drive wheels spaced from each other and free-wheelingly mounted on the first shaft,
   a pair of discharge wheels spaced from each other and fixedly mounted on the second shaft, the drive and discharge wheels being positioned on the respective shafts in a manner that arcs of their respective circumferences cooperate to form a notch-shaped inspection station for seating a substantially cylindrical first object therein, the drive wheels being for driving the object into the inspection station and for imparting a rotary motion to the object during the driving and while the object is seated in the inspection station,
   an infeed cradle mounted above the drive wheels for initially receiving and cradling the infed first object, prior to its being seated in the inspection station,
   sending means synchronized with the rotation of the second shaft, for positively sending the cradled first object from the infeed cradle to the inspection station,
   rotation imparting and deaccelerating means connected to the second shaft and synchronized with the sending means for cooperating with the driving of the drive wheels for imparting a rotary motion to, while simultaneously controlledly deaccelerating the translational motion of, and easing the entry of, the positively sent first object into the inspection station,
   discharge means synchronized with the rotation of the second shaft such that, with each rotation of the second shaft, the discharge means passes through the inspection station and, without use of intermittent motion mechanisms, removes a substantially cylindrical object therefrom and then discharges it from the apparatus,
   means connected to the first and second shafts for rotating them at a constant speed and in time such that the first shaft rotates faster than the second,
   coupling means adjustably mounted on the first shaft and communicating with the drive wheels for connecting them to the first shaft, the coupling means being adjustable to impart certain pre-set desired limited torque driving capabilities to either or both drive wheels in a manner that allows either or both drive wheels to slip with respect to the first shaft when either or both is subjected to a torque whose value exceeds the pre-set limit, and
   detecting means for detecting flaws in each serially fed substantially cylindrical object while it is seated and being rotated in the inspection station.

2. The apparatus of claim 1 wherein the rotation imparting and deaccelerating means and the discharge means is a hook connected to the second shaft, the hook having a convex back surface and a face surface which includes a discharge seat, and the rotation imparting and deaccelerating means being the convex back surface and the discharge means being the face surface.

3. The apparatus of claim 1 wherein the coupling means includes a slip clutch assembly.

4. The apparatus of claim 1 wherein there is included an L-shaped bracket pivotably mounted on a pivot axially parallel to the first shaft, the L-shaped bracket comprising an upstanding body and a leg, and wherein the sending means includes a sending surface on the body, and the infeed cradle is a convex cutout in the leg.

5. The apparatus of claim 4 wherein the L-shaped bracket includes prevent means for preventing a substantially cylindrical second object in an object infeed line above the bracket, from passing to the infeed cradle until the first object has been positively sent therefrom.

6. The apparatus of claim 3 wherein there is included an L-shaped bracket pivotably mounted on a pivot axially parallel to the first shaft, the L-shaped bracket comprising an upstanding body and a leg, and wherein the sending means includes a sending surface on the body, and the infeed cradle is a convex cutout in the leg.

7. The apparatus of claim 6 wherein the L-shaped bracket includes prevent means for preventing a substantially cylindrical second object in an object infeed line above infeed cradle, from passing to the infeed cradle until the first object has been positively sent therefrom.

8. The apparatus of claim 1 wherein there is included hold means for holding a substantially cylindrical object in contact with the drive and discharge wheels and in the inspection station while it is being rotated and inspected therein.

9. The apparatus of claim 8 wherein the object to be inspected is made of a ferrous material, and the hold means includes a primary magnet positioned below the inspection station.

10. The apparatus of claim 9 wherein the hold means includes a secondary magnet positioned between the drive wheels and below their upper peripheral portions, for holding the first object in contact with the drive wheels and the rotation imparting and deaccelerating means while it is being positively sent from the infeed cradle to the inspection station.

11. The apparatus of claim 6 wherin the object to be inspected is made of a ferrous material, and wherein the hold means includes a primary magnet positioned below the inspection station.

12. The apparatus of claim 2 wherein the hook face surface includes cushioning means for cushioning the impact of the face surface upon each object that is removed from the inspection station.

13. The apparatus of claim 9 wherein the primary magnet has an axis which has a north pole at one of its ends and a south pole at the other of its ends, which axis extends in the same direction as but is shorter than the axis of the object, such that the magnet induces a magnetic field through portions of the object which extend axially beyond the respective magnet poles, and wherein the detecting means includes a magnetic sensor positioned beyond the axial length of the permanent magnet in substantial alignment with and in the magnetic field which would emanate from, the rim portion of the object, for detecting a disturbance in the emanated magnetic field caused by a flaw associated with the rim portion of the object.

14. The apparatus of claim 3 including a primary magnet operatively positioned with respect to the inspection status wherein the object to be inspected is made of a ferrous material, wherein the primary magnet has an axis having north and south poles at its ends, which axis extends in the same direction as but is shorter than the axis of the object, such that the magnet induces a magnetic field through portions of the object which extend axially beyond the respective magnet poles, and wherein the detecting means includes a magnetic sensor mounted beyond the axial length of the primary magnet in substantial alignment with an in the magnetic field which would emanate from the rim portion of the object, for detecting a disturbance in the emanated magnetic field caused by a flaw associated with the rim portion of the object.

15. The apparatus of claim 4 wherein including a primary magnet positioned below the inspection station wherein the object to be inspected is made of a ferrous material, wherein the primary magnet has an axis having north and south poles at its ends, which axis extends in the same direction as but is shorter than the axis of the object, such that the magnet induces a magnetic field through portions of the object which extend axially beyond the respective magnet poles, and wherein the detecting means includes a magnetic sensor mounted beyond the axial length of the primary magnet in substantial alignment with and in the magnetic field which would emanate from the rim portion of the object, for detecting a disturbance in the magnetic field caused by a flaw associated with the rim portion of the object.

16. The apparatus of claim 15 including hold means wherein the hold means includes a secondary magnet positioned between the drive wheels below their upper peripheral portions, for holding the first object in contact with the drive wheels and the rotation imparting and deaccelerating means as the object is being positively sent from the infeed cradle to the inspection station.

17. The apparatus of claim 1 wherein the detecting means is axially aligned with and fixedly mounted in a straight line drawn from the center of the inspection station corresponding to the axis of the object to be inspected when said object is operatively positioned in said inspection station to the axis of one of the first and second shafts adjacent the point of contact between the object and one of the wheels mounted on said one of said first and second shafts to maintain a substantially uniform gap between the detecting means and the object.

18. The apparatus of claim 13 wherein the detecting means is axially aligned with and fixedly mounted in a straight line drawn from the center of the inspection station corresponding to the axis of the object to be inspected when said object is operatively positioned in said inspection station to the axis of one of the first and second shafts adjacent the point of contact between the object and one of the wheels mounted on said one of said first and second shafts to maintain a substantially uniform gap between the detecting means and the object.

19. The apparatus of claim 1 wherein there is included orienting means for axially orienting each object fed into the inspection station, the orienting means being in a position such that while the object is in the inspection station, portions of the object which are to be inspected are oriented with respect to and inspectable by the detecting means.

20. The apparatus of claim 1 including orienting means wherein the orienting means includes a surface abutting the edge of and vertical to the inspection station, and a magent for attracting an end of the object in the inspection station to the abutting surface to align the rim edge of the object with the detecting means.

21. An inspection apparatus for detecting flaws in the rim portion of each of a plurality of serially fed substantially cylindrical objects, which comprises:
rotatable first and second shafts parallel to and spaced from each other,
a pair of drive wheels spaced from each other and free-wheelingly mounted on the first shaft,
a pair of discharge wheels spaced from each other and fixedly mounted on the second shaft, the drive and discharge wheels being positioned on the respective shafts in a manner that arcs of their respective circumferences cooperate to form a notch-shaped inspection station for seating a substantially cylindrical first object therein, the drive wheels being for driving the object into the inspection station and for imparting a rotary motion to the object during said driving and while the object is seated in the inspection station,
an infeed cradle mounted above the drive wheels for initially receiving and cradling the infed first object prior to its being seated in the inspection station,
sending means synchronized with the rotation of the second shaft, for positively sending the cradled first object from the infeed cradle to the inspection station,
a hook connected to the second shaft and whose passage through the inspection station during rotation of the second shaft, is synchronized with the sending means, the hook protruding beyond the circumference of the discharge wheels and having a convex back surface for cooperating with the driving of the drive wheels for imparting a rotary motion to, while simultaneously deaccelerating the translational motion of, and easing the entry of the positively sent first object into the inspection station, the hook also having a face surface which includes a discharge seat which passes through the inspection station and removes a substantially cylindrical object from the inspection station before the seating therein of the positively sent, deaccelerated first object, and then discharges the removed object from the apparatus, means connected to the first and second shafts for rotating them in time such that the first shaft rotates faster than the second, coupling means adjustably mounted on the first shaft and communicating with the drive wheels for connecting the drive wheels to the first shaft, the coupling means being adjustable to impart certain pre-set desired limited torque driving capabilities to either or both drive wheels in a manner that allows either or both drive wheels to slip with respect to the first shaft when either or both is subjected to a torque whose value exceeds the pre-set limit, and hold means for holding an object in the inspection station while it is being rotated therein, and detecting means for detecting flaws associated with the rims of each serially fed substantially cylindrical object while it is seated and being rotated in the inspection station.

22. The apparatus of claim 21 wherein the coupling means includes slip clutch means.

23. The apparatus of claim 22 wherein there is included an L-shaped bracket pivotably mounted on a pivot axially parallel to the first shaft, the L-shaped bracket having an upstanding body and a leg, the sending means being a sending surface on the body and the infeed cradle being a convex cutout in the leg.

24. The apparatus of claim 23 wherein there is included prevent means for preventing a second substantially cylindrical object in and object infeed line above the infeed cradle from passing to the infeed cradle until the first object has been positively sent therefrom, and wherein the L-shaped bracket body includes a head, and the prevent means is the head.

25. The apparatus of claim 21 wherein the object to be inspected is made of a ferrous marerial, the hold means includes a primary magnet positioned adjacent the inspection station, the primary magnet having north and south poles at the ends of its axis, which extends in the same direction as but is shorter than the axis of the object, such that the primary magnet induces a magnetic field through portions of the object which extend axially beyond the respective magnet poles, and wherein the detecting means includes a magnetic sensor mounted beyond the axial length of the permanent magnet in substantial alignment with and in the magnetic field which would emanate from the rim portion of the object, for detecting a disturbance in the magnetic field caused by a flaw associated with the rim portion of the object.

26. The apparatus of claim 25 wherein the sensor is axially aligned with and fixedly mounted in a straight line drawn from the center of the inspection station corresponding to the axis of the object to be inspected when said object is operatively positioned in said inspection station to the axis of one of the first and second shafts adjacent the point of contact between the object and one of the wheels mounted on its corresponding shaft to maintain said alignment and a substantially uniform gap between the detecting means and the rim portion of the object, and wherein the inspection apparatus includes orienting means for axially orienting each object fed into the inspection station, the orienting means being in a position such that while the object is in the inspection station, the rim portions of the object are oriented with respect to and inspectable by the magnetic sensor.

27. The apparatus of claim 26 wherein the orienting means includes a surface abutting the edge of and vertical to the inspection station, and a magnet for attracting the end of an object in the inspection station to said surface to align the rim edge of the object with the magnetic sensor.

28. An inspection apparatus for inspecting and detecting flaws in each of a plurality of serially fed substantially cylindrical ferrous objects, which comprises:

rotatable first and second shafts parallel to and spaced from each other, a pair of drive wheels spaced from each other and free-wheelingly mounted on the first shaft, a pair of discharge wheels spaced from each other and fixedly mounted on the second shaft, the drive and discharge wheels being positioned on the respective shafts in a manner that arcs of their respective circumferences cooperate to form a notch-shaped inspection station for seating a substantially cylindrical ferrous first object therein, the drive wheels being for imparting a rotary motion to it while it is seated in the inspection station, an L-shaped bracket having an upstanding body and a leg, including an infeed cradle positioned above the drive wheels for initially receiving and cradling the infeed first object prior to its being seated in the inspection station, and the body having a sending surface for positively sending the cradled first object from the cradle to the inspection station, the bracket being pivotably mounted on a pivot axially parallel to the first shaft, and being synchronized to pivot in time with the rotation of the second shaft, a hook connected to the second shaft and whose passage through the inspection station during rotation of the second shaft is synchronized with movement of the sending surface, the hook protruding beyond the circumference of the discharge wheels and having a convex back surface for cooperating with the driving of the drive wheels for imparting a rotary motion to, while simultaneously deaccelerating the translational motion of, and easing the entry of the positively sent first object into the inspection station, the hook also having a face surface which includes a discharge seat, which passes through the inspection station, and removes a substantially cylindrical object from the inspection station before the seating therein of the positively sent, deaccelerated first object, and then discharges the removed object from the apparatus, means connected to the first and second shafts for rotating them in time such that the first shaft rotates at a higher rate of speed than the second, slip clutch means adjustably mounted on the first shaft and communicating with the drive wheels for connecting the drive wheels to the first shaft, the coupling means being adjustable to impart certain pre-set desired limited torque driving capabilities to either or both drive wheels in a manner that allows either or both drive wheels to slip with respect to the first shaft when either or both is subjected to a torque whose value exceeds the pre-set limit, and hold means for holding the object in contact with the drive and discharge wheels and in the inspecting station while it is being rotated therein, the hold means including a primary magnet positioned below the inspection station, the primary magnet having north and south poles at the respective ends of its axis which extends in the same direction as but is shorter than the axis of the object, such that the primary magnet induces a magnetic field through portions of the object which extend axially beyond the respective magnet poles, detecting means for detecting flaws in the rim of each serially fed ferrous object while it is seated and being rotated in the inspection station, and orienting means for axially orienting each object fed into the inspection station, the orienting means being in a position such that while the object is in the station, the rim portion of the object to be inspected is oriented with respect to and inspectable by the detecting means.

29. The apparatus of claim 28 wherein the detecting means is axially aligned and fixedly mounted in a straight line drawn from the center of the inspection station corresponding to the axis of the object to be inspected when said object is operatively positioned in said inspection station to the axis of one of the first and second shafts adjacent to the point between the object and one of the wheels mounted on said one of said first and second shafts to maintain a substantially uniform gap between the detecting means and the rim portion of object.

30. The apparatus of claim 29 wherein the orienting means includes a surface abutting the edge of the inspection station, and a magnet for attracting an end of the object in the inspection station to said surface to align the rim edge of the object with the detecting means.

31. The apparatus of claim 39 wherein the hold means includes a secondary magnet positioned between the drive wheels below their upper peripheral portions, for holding the first object in contact with the drive wheels and the hook convex back surface as the object is being positively sent from the infeed cradle to the inspection station.

32. A method of providing a substantially uniform gap between detection means and a substantially cylindrical object while it is being rotated in an inspection station formed by portions of the arcs of the circumferences of a pair of drive wheels mounted on a rotatably driven first shaft, and a pair of wheels mounted on a rotatably dirven second shaft parallel to the first shaft, which comprises;

maintaining the substantially cylindrical object in contact with the circumference of the wheels, fixedly mounting the detection means in axial alignment in a straight line to the center of the inspection station corresponding to the axis of the object to be inspected when said object is operatively positioned in said inspection station and to the axis of one of said shafts and wherein the maintaining step is effected by rotatably driving the object into the inspection station by rotating the first shaft faster than the second shaft, and providing hold means for holding the object in contact with the wheels while it is rotating in the inspection station, adjustably mounting coupling means in the first shaft for connecting the drive wheels to the first shaft, employing the coupling means for imparting a certain torque driving capability to either or both of the drive wheels, presetting the limit of the torque, and, allowing either or both drive wheels to slip with respect to the first shaft when it is subjected to a torque whose value exceeds the pre-set limit.

* * * * *